US00PP30940P3

(12) United States Plant Patent
Hansen

(10) Patent No.: US PP30,940 P3
(45) Date of Patent: Oct. 15, 2019

(54) ***NEPETA* PLANT NAMED 'KITTEN AROUND'**

(50) Latin Name: ***Nepeta* x *faassenii***
Varietal Denomination: Kitten Around

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 160 days.

(21) Appl. No.: 15/732,459

(22) Filed: Nov. 15, 2017

(65) Prior Publication Data

US 2019/0150348 P1 May 16, 2019

(51) Int. Cl.
*A01H 5/02* (2018.01)
*A01H 6/50* (2018.01)
*A61K 36/53* (2006.01)

(52) U.S. Cl.
USPC ..... Plt./263.1
CPC ..... *A01H 6/50* (2018.05); *A61K 36/53* (2013.01)

(58) Field of Classification Search
USPC ..... Plt./263.1
CPC ..... A01H 5/02
See application file for complete search history.

*Primary Examiner* — Kent L Bell

(57) ABSTRACT

The new and distinct hardy perennial plant, *Nepeta* 'Kitten Around', has rounded, very short and compact habit with mostly upright stems. The foliage is small, serrate and fragrant. Flowers are a periwinkle blue with persistent rosy-purple calyces. The new plant reblooms heavily if trimmed after initial flowering.

1 Drawing Sheet

Botanical denomination: *Nepeta* x *faassenii*.
Variety designation: 'Kitten Around'.

BACKGROUND OF THE INVENTION

The present invention relates to a new and distinct cultivar of *Nepeta* named 'Kitten Around'. The new plant resulted from a cross between *Nepeta* 'Purrsian Blue' U.S. Plant Pat. No. 24,788 as the female or seed parent and *Nepeta* 'Psfike' U.S. Plant Pat. No. 18,904 as the male or pollen parent directed by the inventor on Jun. 12, 2012. Seed was harvested Aug. 7, 2012 and eventually assigned the breeder code 12-2-2 toward the end of the trial period. 'Kitten Around' was approved in a final evaluation in the summer of 2015 and slated for later introduction. The new plant was selected based on the compact habit and repeat blooming following trimming. The new plant has been asexually propagated by tip cuttings with the resultant plants remaining identical to the original plant, stable and true to type in successive generations.

SUMMARY OF THE INVENTION

*Nepeta* 'Kitten Around' is different from its parents and all other Catmint known to the inventor. In comparison to the female parent, 'Purrsian Blue', the new plant is more compact and shorter. Compared to the male parent, 'Psfike', the new plant is also shorter and more compact. The nearest comparison varieties are *Nepeta* 'Novanepjun' U.S. Plant Pat. No. 23,074, more commonly known as 'Junior Walker'. Compared with 'Novanepjun' the new plant is more compact with smaller leaves and habit. Compared with 'Walker's Low' (not patented) the new plant is less than one-half the landscape size and is more compact. In comparison to 'Blue Dragon' U.S. Plant Pat. No. 22,334, 'Cat's Meow'

U.S. Plant Pat. No. 24,472, and 'Summer Magic' U.S. Plant Pat. No. 27,090 the new plant is more compact and shorter than each.

The present invention has not been evaluated under all possible environmental conditions. The phenotype may vary with changes in the environment such as light, temperature, water and nutrient availability, etc. without a change in the genotype of the plant. *Nepeta* 'Kitten Around' is unique from all other catmint known to the inventor in the following combined traits:

1. The habit is rounded, very short and compact with mostly upright stems.
2. Foliage is small with serrate teeth and fragrant.
3. Flowers are periwinkle blue with persistent rosy-purple calyces.
4. Plant reblooms heavily if trimmed after initial flowering.

BRIEF DESCRIPTION OF THE DRAWINGS

The photographs of the new plant *Nepeta* 'Kitten Around' are of a two-year old plant in a full-sun, trial garden in Zeeland, Mich. and demonstrate the unique aspects of the new plant. The colors are as accurate as reasonably possible with color reproductions. Ambient light spectrum, temperature, source and direction may cause the appearance of minor variation in color.

DETAILED PLANT DESCRIPTION

Figure 1:
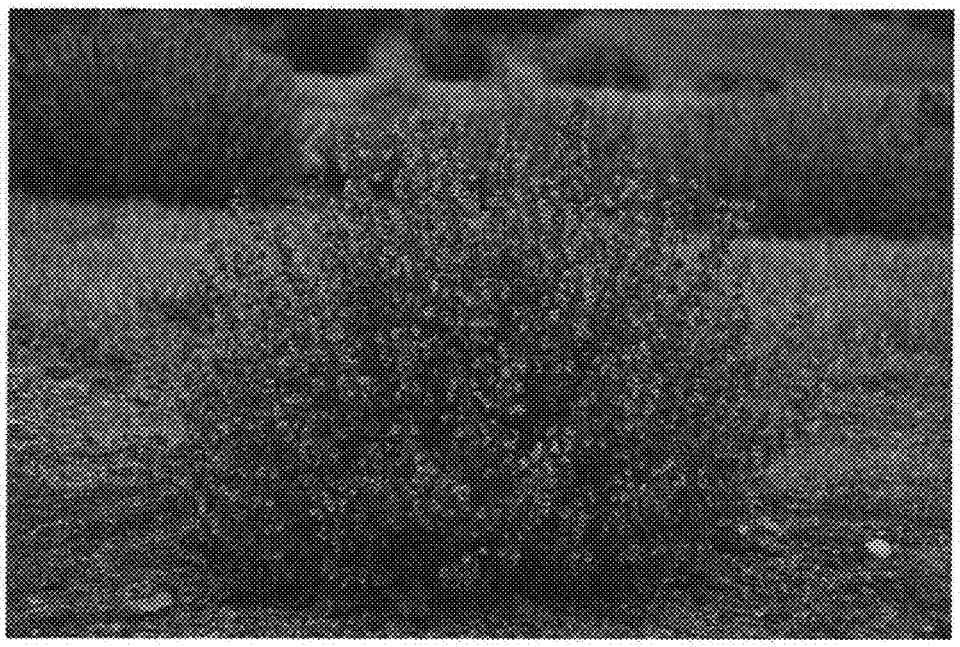
FIG. 1 shows the overall habit of *Nepeta* 'Kitten Around'.
Figure 2:
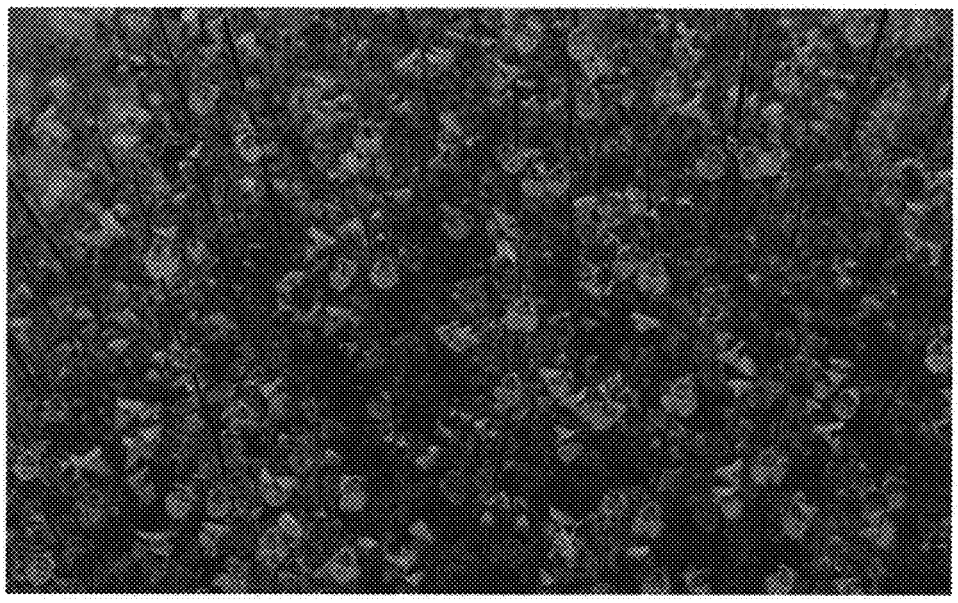
FIG. 2 shows a close-up of the flowers, buds and stems.

The following descriptions are based on a two-year old plant of *Nepeta* 'Kitten Around' grown in a full-sun trial garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: 'Purrsian Blue' as the female or seed parent, the male or pollen parent was 'Psfike';

Plant habit: Herbaceous perennial; upright mounding to about 28 cm tall and 42 cm wide at the base in flower;

Growth: Rapid; time to initiate roots at 23° C. about one week; finishing in a standard #1-15 cm container in about 8 to 10 weeks from rooted 25 mm plug;

Root: Fine, freely branching; color nearest RHS 158D depending on soil type and nutrient content;

Foliage: Opposite; simple; ovate; rugose on both abaxial and adaxial surfaces; margins serrate with about 10 teeth per side; finely puberulent on abaxial and adaxial surfaces; apex broadly acute; base rounded; blade size to about 29.0 mm long and 21.0 mm wide, average about 21.0 mm long and 15 mm across;

Foliage fragrance: Foliage and stem herbal fragrance;

Venation: Longitudinal; impressed on adaxial surface and ribbed on abaxial surface;

Vein color: Adaxial nearest RHS 137C and abaxial between RHS 146B and RHS 146C;

Leaf color: Young expanding adaxial nearest RHS 138A, young expanding abaxial nearest RHS 138B; mature adaxial nearest RHS 137A, mature abaxial nearest RHS 147B;

Petiole: Pubescent adaxial and abaxial; concavo-convex; to about 9.0 mm long and 1.5 mm across at base; average about 6.0 mm long and about 1.2 mm across;

Petiole color: Adaxial nearest RHS 146B, abaxial nearest RHS 146C;

Stem: Pubescent, quadrangular, about 30.0 cm long and 3.0 mm across at base; about 30 stems per plant; branched in upper 6 nodes; 12 branches per stem, branches to about 10.5 cm long and 1.2 mm across at base;

Stem color: Lower portion nearest RHS 146B, upper portion nearest RHS 146A blushed with nearest RHS N186C to solid RHS N186C;

Internodes: Average about 3.3 cm apart with greatest distance in the middle of the stem; about 8 nodes per stem before flowers, branched in upper 6 nodes;

Internode color: Same as surrounding stem;

Inflorescence: Cymosely clustered with many flowers either sessile or branched at verticillasters in the 6 upper nodes; about 9 to 20 flowers per node and about 50 to 100 flowers per inflorescence stem or peduncle;

Peduncle: Mainly vertical; flower portion in distal 6.5 cm and 3.5 cm wide,

Pedicel: Sessile;

Flower bud: Curved clavate; about 9.0 mm long and 4.5 mm wide at the widest point one day prior to opening; adaxial surface pubescent;

Flower bud color: Petal portion nearest RHS 86B distally and nearest RHS N87D near calyx; calyx portion nearest RHS 139B with tinting of between RHS N186D and RHS 187B;

Flowers: Zygomophic; perfect; bilabiate; sympetalous with basal 10.0 mm fused; synsepalous; lips opening to form about 120 degree angle to each other; 13.0 mm long and 10.0 mm across broadest face; in dense verticillasters;

*Upper lip*.—With two lobes; puberulent on basal two-thirds of abaxial surface, glabrous distally and adaxial; lobes about 2.0 mm long and 2.0 mm wide above fusion; lobes with rounded apex; total size of lip about 11.0 mm long and about 5.0 mm wide at fusion.

*Lower lip*.—Consisting of three lobes; center and largest lobe concave to flattened with rounded apex and crenate margin; two side lobes with rounded apices and entire margin; center lobe to 5.0 mm long from fusion and 5.0 mm across; side lobes 2.0 mm long from fusion and 3.0 mm across; puberulent abaxial, glabrous adaxial except pubescent tuft of white hairs nearest NN155D about 2.0 mm long outside fusion of two lips.

*Petal color*.—Adaxial face upper and lower lips nearest RHS N88C with marginal rim nearest RHS N87C; adaxial tube nearest RHS 84D with spots in semicircle in proximal tube mouth between RHS 83A and RHS 83B; abaxial upper face nearest RHS N87C with marginal rim nearest RHS N87A; abaxial tube between RHS N87C and RHS N87D.

Calyx: Synsepalous, 5-merous fused into tube in basal 4.0 mm and separated in distal 2.0 mm; about 6.0 mm long and 2.5 mm diameter;

Sepals: Five; acute apex, base fused; with about 3 conspicuous longitudinal veins; pubescent adaxial, glabrous abaxial; persistent; about 6.0 mm long and 1.0 mm across at fusion;

Sepal color: Adaxial between veins nearest RHS 145C and veins nearest RHS 146A, in regions of high light blushed nearest RHS N186C; abaxial nearest RHS 145C with veins nearest RHS 146A and in high light nearest RHS 187B with veins blushed nearest RHS N186C;

Gynoecium: Single compound ovary with two carpels, single gynobasic style, and stigma split in two parts;

*Style*.—About 12.0 mm long and 0.5 mm diameter; color basal one-half between RHS 71A and RHS 72A, distally lightening to nearest RHS 76B.

*Stigma*.—Bifid in distal 1.0 mm to sharply acute apex; color nearest RHS 83A.

*Ovary*.—Four-lobed, each lobe ovoid, about 1.0 mm long and 0.5 mm across, ovary color between RHS 145A and RHS N144D.

Androecium: Four;

*Filaments*.—Adnate to petals, free in distal 4.0 mm terete; color nearest RHS N87B.

*Anthers*.—Oblong ellipsoidal; 1.0 mm long and 0.5 mm diameter; color nearest RHS N186A.

*Pollen*.—Abundant; color nearest RHS 158B.

Flowering period: In Western Michigan beginning early June for six weeks and repeating into October if trimmed back; individual flowers remain open for up to three days;

Flower fragrance: None detected;

Flower attitude: Outwardly;

Fruit and seed: Rare, nutlets, flattened, round; about 1.5 mm diameter and 0.5 mm thick; nearest RHS 200B;

Pest and disease susceptibility: No resistance beyond that which is typical for *Nepeta* but typically not prone to browsing by deer or rodents.

I claim:

1. A new and distinct hardy perennial *Nepeta* plant, named 'Kitten Around' essentially as herein described and illustrated useful for landscaping as a specimen, en masse, or in a container to bring color and fragrance to a garden and attract butterflies and hummingbirds.

* * * * *